United States Patent [19]
Hughes, Jr. et al.

[11] Patent Number: 5,942,539
[45] Date of Patent: Aug. 24, 1999

[54] METHODS OF TREATING OR PREVENTING ENDOMETRIOSIS WITH PHYTOESTROGENS

[75] Inventors: Claude L. Hughes, Jr., Simi Valley, Calif.; J. Mark Cline, Winston-Salem, N.C.; Thomas B. Clarkson, Clemmons, N.C.; Daniel B. Whitesides, Charlotte, N.C.

[73] Assignee: Wake Forest University, Winston-Salem, N.C.

[21] Appl. No.: 08/943,559

[22] Filed: Oct. 3, 1997

[51] Int. Cl.⁶ ..................................... A61K 31/35
[52] U.S. Cl. .................. 514/456; 514/455; 514/453; 514/874; 514/15; 514/473; 514/169; 514/172
[58] Field of Search ............................... 514/15, 456, 455, 514/453, 874, 473, 104, 172

[56] References Cited

U.S. PATENT DOCUMENTS

5,424,331  6/1995  Shlyankevich ........................... 514/456

*Primary Examiner*—James H. Reamer
*Attorney, Agent, or Firm*—Pat Winston Kennedy; Kilpatrick Stockton LLP

[57] ABSTRACT

Methods of using phytoestrogens, in particular, isoflavones in the prevention and treatment of endometriosis and related disease conditions in females. One method comprises administering a therapeutically effective dosage of a phytoestrogen to females with endometriosis, females having symptoms related to endometriosis, or to females at risk of developing or suffering recurrence of endometriosis. In another method, at least one phytoestrogen may be administered singly or in combination with at least one hormonal therapeutic agent such as GnRH analogs, androgens, progestins, estrogens or any combination thereof. The therapeutically effective dosage of the phytoestrogen or the combination therapeutic ranges between about 25 and about 250 mg/day.

25 Claims, 3 Drawing Sheets

METHODS OF TREATING OR PREVENTING ENDOMETRIOSIS WITH PHYTOESTROGENS

BACKGROUND OF THE INVENTION

The present invention relates to methods of treating and preventing endometriosis in adult females using phytoestrogens. More particularly, the present invention relates to methods of using phytoestrogens, in particular, isoflavones singly or in combination with other hormonal therapeutic agents to prevent endometriosis in females at risk for the disease as well as to treat those females with the disease or symptoms associated therewith.

Endometriosis is a common and debilitating disease of adult women in their 20's and 30's in which functional endometrial tissue is present and growing in areas outside the uterus, in particular the peritoneal cavity. As a result, severe pain often occurs in response to the hormonal changes that take place during the female menstrual cycle. Even more devastating is the infertility that frequently occurs due to the abnormal growth and accumulation of endometrial tissue on organs outside of the uterus.

At present, endometriosis is routinely treated with a variety of hormonal therapies, which include gonadotropin-releasing hormone analogs ("GnRH analogs"), danazol, progestins, and continuous high-dose oral contraceptives. Each of these therapies has similar response rates in terms of diminished pelvic pain and laparoscopically demonstrated extent of disease. However, the effectiveness of each current treatment option is compromised by severe side effects and/or major health concerns experienced by many women.

For example, GnRH analogs such as Lupron inhibit ovarian production of estradiol, resulting in symptoms and health risks associated with estrogen deprivation.

Further, prolonged use of these analogs (more than twice in a lifetime for six months at a time) leads to bone loss. Danazol, an androgen, inhibits ovarian production of estradiol, and acts as a pharmaceutical androgen. This results in symptoms of androgen excess (masculine side effects) and risks of estrogen deprivation. Progestins are poorly tolerated by women due to their effects on mood, fluid retention and breast tenderness. When consumed alone in high doses, progestins inhibit ovarian estrogen production, and also have an adverse impact on plasma lipids. Further, high dose-continuous use of oral contraceptives to produce a "pseudopregnancy state" causes irregular vaginal bleeding, hyperemesis, fluid retention and weight gain as well as increases the risk of acute thromboembolic events. Additionally, the long-term consequences of each of these current therapies pose serious health concerns, particularly in view of known increased risks of atherosclerosis, osteoporosis, or both, especially in individuals requiring repetitive courses of treatment for endometriosis due to recurrent disease.

In determining the hormonal effects of various compounds on female organs, a co-inventor of the present invention studied the effects of soy isoflavones on endometrium in women. Isoflavones are an important class of naturally-occurring phytoestrogens, whereas soy isoflavones are derived from soybeans, a particularly important source of phytoestrogens. Genistein (4',5,7-trihydroxyisoflavone) and daidzein (4'7-dihyroxyisoflavone) are examples of the most potent isoflavones.

The estrogenic actions of dietary "phytoestrogens" (specifically isoflavones) have raised some concerns regarding the potential endometrial stimulatory effects of these compounds in women. On the contrary, demographic observations indicate that several chronic diseases of menopausal women in "Western" nations including endometrial cancer were much less prominent in Pacific Rim nations where traditional diets include substantial intake of soy foods that contained significant quantities of isoflavones. The basic hypothesis of the following studies was that dietary intake of these estrogen-like non-nutritive compounds would substantially account for these differences in disease occurrence. To experimentally address this hypothesis, the effects of the dietary soy isoflavones were studied on markers of risk of endometrial cancer in both rats and monkeys. Presented in great detail below are the unpublished test results along with relevant background material on phytoestrogens.

Phytoestrogens are naturally-occurring constituents in many plants. Legumes are particularly rich in estrogenic isoflavones and coumestans, while grains are rich in estrogenic lignans. Isoflavones affect mammalian physiology via several mechanisms including estrogen receptor agonism and possible antagonism, plus receptor-independent antioxidant properties and inhibition of several enzymes involved in cell-signaling and proliferation. Since several chronic diseases of menopausal women (including breast cancer, colon cancer and atherosclerotic cardiovascular disease) in "Western" nations are much less prominent in Pacific Rim nations where traditional diets include substantial intake of soy foods rich in isoflavones, the strengthening hypothesis is that intake of these non-nutritive dietary phytochemicals accounts for these differences in disease occurrence.

Ongoing studies at several centers around the world were assessing the biological bases for the growing enthusiasm regarding the potential beneficial role of these compounds in reducing risk of disease in menopausal women. As part of this study, it was hypothesized that the soy isoflavones might act as mixed estrogen agonist/antagonists; the experimental result from the rats and nonhuman primates (monkeys) showed evidence to that effect. The results demonstrated 1) either no stimulation or weak agonism; and 2) antagonism of steroidal estrogen-induced proliferation of endometrium in both animal models.

Structure and Occurrence of Phytoestrogens

Dietary phytoestrogens are naturally-occurring constituents of plants that elicit estradiol-like effects in one or more target tissues in animals. Nearly 70 years ago, it was discovered that certain plants could induce estrus in animals. Subsequently, after adoption of bioassay methods that assessed vaginal or uterine effects of putative estrogens, over 300 plants were found to possess some degree of estrogen-like activity. These phytoestrogens are predominantly from two chemical classes (coumestans and isoflavones) and their metabolites, such as equol. The isoflavones and coumestans have 15 carbon structures similar to the 17-carbon structure of estradiol.

The richest sources of isoflavones among foodstuffs are legumes and grains, with soy content of the isoflavones genistein, daidzein and their conjugates on the order of 0.5 to 3 mg/gram of soy protein. For human health considerations, a focus on the isoflavones from soybeans was justifiable due to the fact that consumption of soybeans and soyfood products is increasing, and soybeans are the major source of genistein and daidzein in human diets.

In humans, dietary phytoestrogens are readily absorbed, circulate in the plasma and are excreted in the urine. The plasma levels range up to hundreds of nmol/L in persons consuming diets that are rich in these compounds.

Mechanisms of Action of Phytoestrogens In Mammals

It is known that estradiol-like effects can be produced by these compounds, and the impact of these actions of phytoestrogens on the reproductive physiology of mammals can be quite prominent. Multiple studies in rats and mice show uterotrophic effects which may be estrogenic or anti-estrogenic in nature depending upon the experimental design. Extensive studies in sheep demonstrate either transient or permanent alterations in the female genital tract including morphological and biochemical changes of the cervix [Adams, N. R., *Proc Soc Expl Biol Med* 208:87 (1995)] and the uterus [Tang, B. Y. et al., *J Endocrinol.* 89:365 (1981); Tang, B. Y. et al., *Austr J Biol Sci* 35:527 (1982)] which can credibly explain reversible and irreversible loss of fertility. Limited trials in women [Wilcox, G. et al., *BMJ* 301:905 (1990); Baird, D. D. et al., *J Clin Endocrinol Metab* 80:1685 (1995)] and monkeys [Hughes, C. L. et al., Abstr, *Third International Conference on Phytoestrogens*, Little Rock, Ark. (1995); Cline, J. M. et al., *Fertil Steril* 65:1031 (1996)] suggest that phytoestrogens elicit minimal estrogenic effects on the maturation of vaginal epithelium and do not antagonize the actions of steroidal estrogens on the vagina.

On the other hand, preliminary work by one of the co-inventors suggests that stimulation of some estrogen-dependent histochemical and histomorphometric markers in the uterus by dietary steroidal estrogens is diminished by concurrent inclusion of soy phytoestrogens in the diet [Tansey, G. et al, *Proc Soc Expl Biol Med*, in press (1997)]. The implication is that the patterns of effect may not be simply that of a weak estrogen agonist. Although these phytochemicals might affect mammalian reproductive physiology solely by mimicry of estradiol via estrogen receptors, there is no a priori justification for assuming that all mammalian reproductive effects of these compounds will be estrogen receptor-mediated or that observed effects will necessarily be limited to mechanisms that are known to be affected by steroidal estrogens. The possible mechanistic categories are summarized in Table 1 below.

TABLE 1

Possible mechanistic categories of phytoestrogen action in mammals

Phytoestrogens may:

1. have pharmacokinetic and metabolic affects that alter production, patterns of secretion, distribution or metabolism of endogenous sex hormones;
2. act as an agonist at estrogen receptors;
3. act as an antagonist (or mixed agonist/antagonist) at estrogen receptors;
4. have non-receptor mediated estradiol-like actions (as an agonist or antagonist);
5. have no action on particular target tissues or processes; or
6. have effects on particular target tissues or processes that involve non-estrogenic mechanisms "Classical" Estrogen Receptor-Dependent Activity: Many different phytoestrogens have been shown to bind the estrogen receptors (ER) and effect nuclear translocation [Martin, P. M. et al., *Endocrinology* 103:1860 (1978)]. Soy isoflavones have long been recognized as "phytoestrogens" [Price, K. R. et al., *Food Add Contam* 2: 73 (1985)]. Most isoflavones act as weak estrogens in vivo and in vitro. Genistein binds with approximately 1/250th of the affinity of estradiol to the estrogen receptor (ER)[Miksicek, R. J., *J Steroid Biochem Molec Biol* 49:153 (1994)]. Such low affinity binding might explain observations that suggest mixed estrogen agonist/antagonist properties of phytoestrogens [Verdeal, K. et al, *J Nat Cancer Inst* 64:285 (1980)].

"Non-Classical" Receptor-Dependent Activities: Other than the ER, several possibilities have been reported to exist, which might function as alternative receptor-mediated mechanisms for manifestation of phytoestrogen action (see Table 2 below). A specific mechanistic alternative to the ER offers the possibility of rectifying some of the phenomenological differences between observed effects of phytoestrogens and more traditional ER agonists. Furthermore, since phytoestrogens are not endogenous lignans per se within animals, these compounds may not act exclusively through a single mechanism.

TABLE 2

RECEPTOR MEDIATED ESTROGENIC MECHANISMS DISTINCT FROM THE CLASSICAL ER-alpha

1. Estrogen Related Receptors - The DNA sequences of two estrogen-related receptors (ERR1 & ERR2) are distinct from both ER-alpha and ER-beta, but have a high degree of sequence homology. ERR1 has been implicated in regulation of expression of at least one estrogen-responsive gene (lactoferrin). Specific putative ERR1 or ERR2 ligands have not been identified.
2. Estrogen receptor beta - Recently, a second ER was identified, shares high homology with the classical ER (ER-alpha) and binds several known estrogens with high affinity.
3. Heat Shock Protein 90 (HSP90) and the Aryl hydrocarbon (Ah) receptor - HSP90 is a chaperone protein that modulates AhR and ER activity. In the case of the AhR, isoflavones inhibit phosphorylation of HSP90, thus inhibiting dissociation of HSP90 from the receptor and inhibiting transcription of AhR responsive genes. A comparable effect may occur with the ER.
4. Membrane binding - Estradiol appears to be a ligand for the truncated form of the epidermal growth factor receptor (c-erbB2). Extremely rapid induction (within 10 seconds) of protein tyrosine phosphorylation by estradiol in MCF-7 suggests a membrane-mediated effect.

Receptor-Independent Actions of Isoflavones: Isoflavones have been shown to have multiple effects on cellular and biochemical processes that are known to be important in normal mammalian physiology. These actions of isoflavones are summarized below in Table 3.

TABLE 3

CELLULAR AND BIOCHEMICAL ACTIONS OF ISOFLAVONES THAT ARE PRESUMABLY RECEPTOR-INDEPENDENT

The isoflavone genistein has been shown to inhibit the following:

| | |
|---|---|
| 1. | Proliferation |
| 2. | Tyrosine Kinases |
| 3. | DNA topoisomerases I and II |
| 4. | Aromatase |
| 5. | 17 beta-hydroxysteroid oxidoreductase |
| 6. | Ribosomal S6 kinase |
| 7. | Formation of Reactive Oxygen Species and to stimulate |
| 8. | Apoptosis |
| 9. | Prostaglandin H synthase |

Prominent among these are effects on cell proliferation and tyrosine kinases. Genistein is known to suppress the growth of several tumor cell types in culture, such as tumor cells derived from gastrointestinal tract including stomach and colon as well as from breast. Genistein also decreases the expression of the oncogene c-myc in, and inhibits proliferation of, two different colon cancer cell lines. It appears that the anti-proliferative effects of the isoflavones override proliferative tendencies arising from any estrogenic actions, as shown by an increased proliferation of breast cancer cells in vitro at low (estrogenic) doses of genistein [Makela, S. et al, *Env Hlth Perspect* 102:572 (1994)] and inhibition of proliferation at higher doses [Peterson, T. G. et al., *Biochem Biophys Res Comm* 179:661 (1991)].

Genistein modulates signal transduction by alteration of kinase activity, and affects growth factor action. Genistein is a specific inhibitor of tyrosine protein kinases, which in turn play an important role in mediating signal transduction events for growth factors such as epidermal growth factor, insulin, platelet-derived growth factor and insulin-like growth factors. Genistein has been shown to inhibit dioxin-induced down-regulation of the inhibitory growth factor TGF-beta in hepatoma cells, presumably by its tyrosine kinase-inhibiting activity. Furthermore, since there is evidence of antagonism of steroidal estrogen actions by isoflavones [Folman, Y. et al., *J Endocrin* 34:215 (1966)], the report by A. Migliaccio et al. [*Oncogene* 8:2183 (1993)]of extremely rapid induction (within 10 seconds) of protein tyrosine phosphorylation by estradiol in human breast cancer cells (MCF-7) suggests that the antagonistic actions of isoflavones could be independent of the classical ER-mediated transcriptional mechanism.

Endometrial Actions of Phytoestrogens

The reproductive failure in sheep grazed on estrogenic pastures has been largely attributed to the effects of phytoestrogens on the uterus and cervix [Bennetts, H. W. et al., *Aust Vet J* 22:2 (1946)]. These female reproductive tract effects include an increase in thickness and keratinization of vaginal epithelium, enlarged cervix, increased uterine weight, and endometrial hyperplasia, all of which are similar to the changes induced by steroidal estrogens[Adams, N. R. *Proc Soc Expl Biol Med* 208:87 (1995); Nwannenna, A. et al., *Proc Soc Expl Biol Med* 208:92 (1995)]. These estrogenic actions of dietary phytoestrogens have raised concerns regarding the potential endometrial effect of these compounds in women, but the growing evidence of cardioprotective benefits of dietary soybean estrogens in post-reproductive age women provides a clear impetus to assess the effects of these compounds in adult female models of the menopause.

An experimental goal was to assess the actions of soy phytoestrogens (isoflavones) on the adult female genital tract in animal models that mimic the menopausal women. Since there is a spectrum of relative sensitivities among the several available markers of estrogenic bioactivity in the uterus, we supposed that several endpoints of estrogen action should be determined. For example, the classical uterine weight gain effect is rather insensitive, while induction of the uterine secretory protein lactoferrin (Ltf) is an exquisitely sensitive marker of estrogen action in the rodent reproductive tract. It had been previously shown that lactoferrin appears in the uterus of rodents at the lower limits of detectability of estrodiol in the serum. [Walmer, D. K. et al., *Endocrinology* 131:1458 (1992)]. Thus using several markers of estrogenic activity, we assessed the effects of soy isoflavones alone or in combination with commonly used pharmaceutical estrogen preparations, either conjugated equine estrogens (CEE) or estradiol (E2) on the reproductive tract of ovariectomized rats and monkeys. The methods used in the following rat study included immunohistochemical staining for proliferating cell nuclear antigen (PCNA) and lactoferrin (Ltf), uterine weight and body weight, vaginal cytology, and uterine luminal epithelial height (LEH). In the monkey study, Ki-67 was used as the histochemical marker of endometrial proliferation.

Effects of Soy Isoflavones on the Endometrium of Ovariectomized Rats

Materials and Methods: Female Harlan Sprague-Dawley rats (N=127), age 40 days were assigned to 12 study groups. Most rats were ovariectomized and placed on diets containing either casein or soy protein (Low Soy, low dose=11.6 mg isoflavones/1800 cal. diet; High Soy, high dose=117.8 mg isoflavones/1800 cal), with no CEE (Premarin, Wyeth-Ayerst, Radnor, Pa.), low dose CEE (0.313 mg CEE/1800 cal), or high dose CEE (0.625 mg CEE/1800 cal) added. The isoflavone dosages were based on previous work using soybean diets in rats [Washburn, S. A. et al., *Am J Obstet Gynecol* 169:251 (1993)]. Another group of rats were sham ovariectomized, and placed on casein or SBE diets, with no CEE added. Soy isolates were provided by Protein Technologies International (St. Louis, Mo.) as SUPRO 670 and SUPRO 670-IF. The latter is alcohol extracted to reduce the isoflavone content of the soybean isolate to its attainable level (0.173%). All diets were formulated in the Comparative Medicine Clinical Research Center diet laboratory. Rats were maintained under a 14:10 hour light:dark cycle with food and water provided ad libitum.

The animals were fed the diets for two months. Vaginal cytology samples were taken daily for one week at the beginning of diet treatment and one week at the end of the study. Vaginal cytology samples were obtained by aspiration. At the end of the study, animals were euthanized and necropsied. The uteri were collected and fixed overnight in 10% neutral buffered formalin (at 4° C.) and then transferred to 70% ethanol for storage before being processed for paraffin sectioning. Tissue sections were mounted on poly-L-lysine coated slides for PCNA innmunohistochemical staining; other sections were mounted on Probe-on Plus8 charged slides (Fisher Scientific, Pittsburgh, Pa.) for the lactoferrin immunohistochemical staining.

PCNA staining was performed according to a modification of the protocol of Foley et al. [*Environ Health Perspect* 101(suppl. 5):(1994)]. Briefly, the slides were dried overnight, deparaffinized through three changes of xylene, hydrated to distilled water, and incubated with PC-10 antibody (Novocastra Laboratory, Newcastle-on-Tyne, UK) in capillary gap slides at 35° C. for 30 minutes. A link antibody (biotinylated anti-mouse antibody, Biogenex Super-Sensitive7 StrAviGen, Biogenex, San Ramon, Calif.) was applied, and the slides incubated at room temperature for 30 minutes; then the label antibody was applied (SuperSensitive8 Streptavidin Alkaline Phosphatase, Biogenex) and incubated at room temperature for 30 minutes. The chromogen (Alkaline Phosphatase Substrate Kit 1, Vector Laboratories, Burlingame, Calif.) was applied for 15 minutes at room temperature, under dark conditions. Slides were counterstained with Mayer's hematoxylin for 5–10 minutes, and dehydrated to xylene for coverslipping.

Sections were counted using a MacIntosh-based image analysis system, using video acquisition of 40X-magnification color images (VK-C370 camera, Hitachi Corp., Lyndhurst, N.J.; and a Scion LG-3 capture board, Scion Corp., Frederick, Md.), which were then processed using the public domain NIH Image program (written by Wayne Rasband, National Institutes of Health, available from the Intenet by anonymous FTP from zippy.nimh.nih.gov). Using a grid to randomize counting, 100 cells were evaluated based on a modification of the grid-filtering system of Lindholm [*Anal Cell Pathol* 4:443 (1992)], from both the superficial and deep endometrial glands. For the purposes of analysis, cells with any amount of staining were considered positive. The positively stained cells were expressed as a percentage of the total for both superficial and deep glands in each section. Data analysis performed using the JMP statistical program (SAS Institute, Cary, N.C.); means were compared using ANOVA and Student's t-test.

Lactoferrin staining was performed according to the protocol of Walmer et al. (*Endocrinology* 131:1458 (1992)]. Staining intensity scores were assessed by an experienced investigator who was blinded to the identity of each specimen at the time inspection and scoring. Staining of the endometrial epithelium for Ltf was scored as 0 (no visible staining), 1+(weak staining), and 2+(intense staining) of the section.

Results: The addition of CEE to casein or either Soy diet resulted in vaginal smears which were similarly estrogenized (data not shown). Neither Low nor High Soy isoflavone diets had any effect upon vaginal cytology, relative to the casein controls. While CEE inhibited the expected ovariectomy-related gain in body weight and increased uterine weight, isoflavones alone at either low or high doses had no effect (data not shown). The interaction of isoflavones and CEE resulted in body weights similar to those of animals fed CEE alone.

Figure 1:
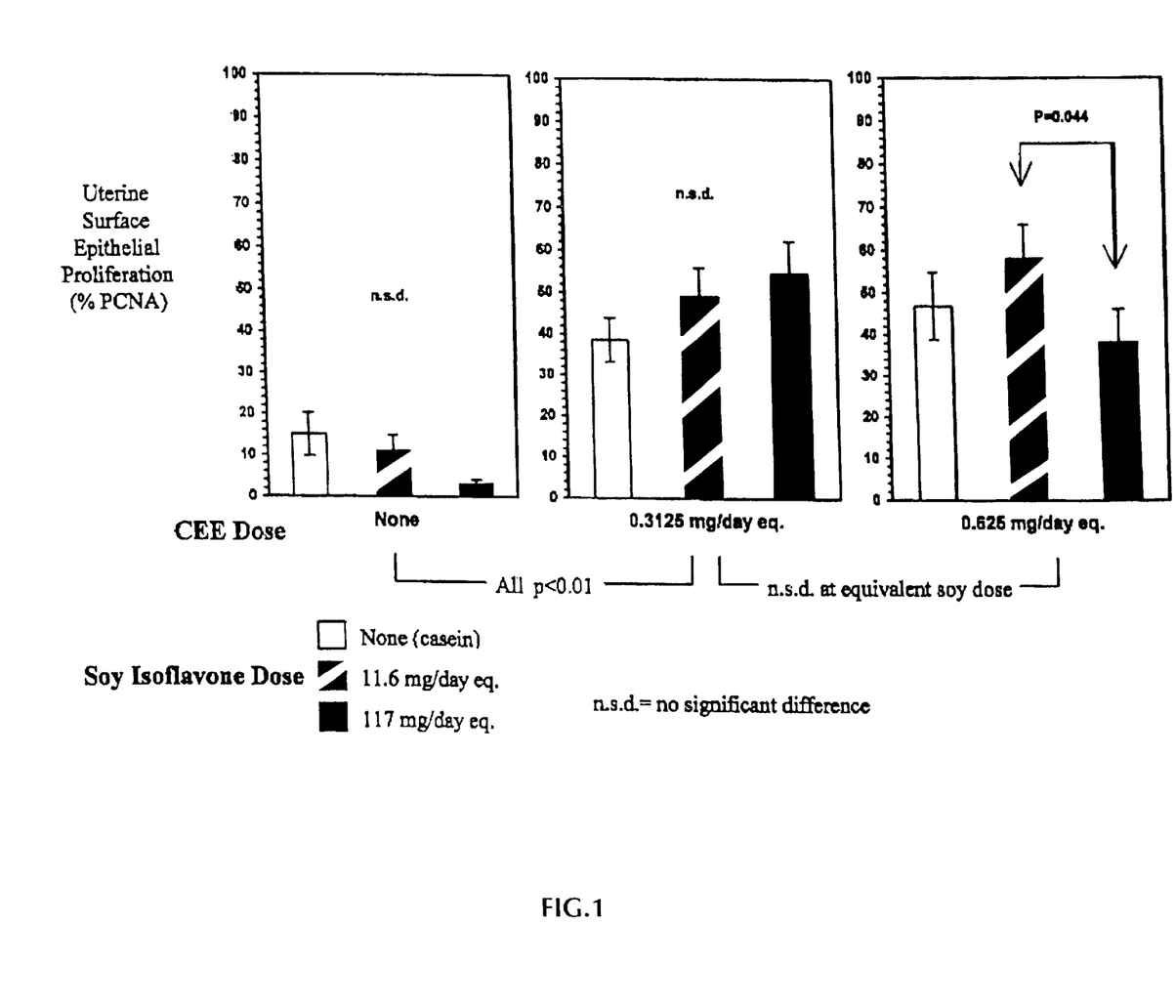
FIG. 1 illustrates the effects of CEE and soy isoflavones on rat uteri: proliferating cell nuclear antigen (PCNA) staining of endometrial surface cells (unpublished test results). Error bars indicate the standard error of the mean. Stained cells are expressed as a percentage of the total cells counted in each section.
Figure 2:
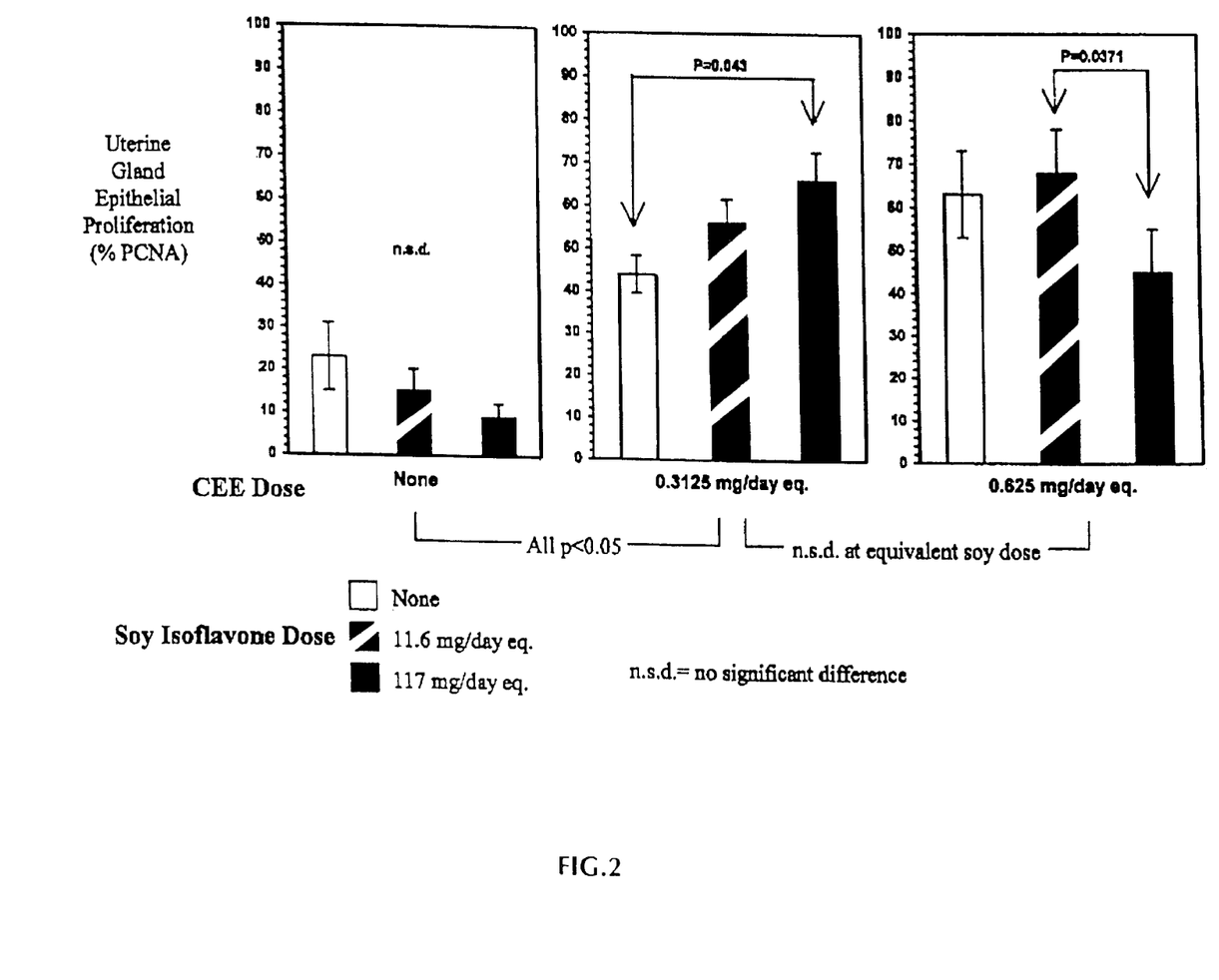
FIG. 2 also illustrates the effects of CEE and soy isoflavones on rat uteri: proliferating cell nuclear antigen (PCNA) staining of endometrial glands (unpublished test results). Error bars indicate the standard error of the mean. Stained cells are expressed as a percentage of the total cells counted in each section.

In all three diet groups with no CEE exposure, proliferating cell nuclear antigen (PCNA) staining showed low levels of proliferation (see first panels in FIGS. 1 and 2). The addition of CEE to all three diets resulted in a significant increase in proliferation (p<0.05 or p<0.01).

Surface Endometrial Cells: In comparison to groups with no CEE exposure (FIG. 1, first panel), exposure to the low dose of CEE (FIG. 1, second panel) increased PCNA staining. No interactive effect of low or high isoflavones was detected. In groups exposed to high CEE (FIG. 1, third panel), a distinct significant inhibitory (antagonistic) effect of high isoflavones was found.

Endometrial Glands: In comparison to groups with no CEE exposure(FIG. 2, first panel), exposure to the low dose of CEE (FIG. 2, second panel) increased PCNA staining. The low CEE + high isoflavone group was significantly greater than the low CEE alone group, suggesting additive agonist effects at these doses. The low CEE + low isoflavone group was intermediate. In groups exposed to high CEE (FIG. 2, third panel), a distinct significant inhibitory (antagonistic) effect of high isoflavones was found.

The results of immunohistochemical staining of cross sections of rat uteri for Ltf are shown in Table 4 below. As expected, the potent CEE induced high levels of Ltf expresslon in 78% of uteri. However, 73% of rats fed the casein diet exhibited low (1+) levels of Ltf expression, suggesting that there are at least trace amounts of bioactive estrogen(s) in that diet even though none of the constituents were expected a priori to have provided consequential amounts of estrogen (s). Remarkably, neither the low or high levels of dietary isoflavones used in this study induced any detectable Ltf expression. Additionally, the potent induction of Ltf by treatment with either dose of CEE was substantially reduced by both the high and low isoflavone diets (see Table 4). Even with the low isoflavone diet, the reduction of the stimulatory effect of either high or low doses of CEE was obvious with 2+ staining limited to only 20% of the uteri.

TABLE 4

Effects of CEE and Soy isoflavones on lactoferrin (Ltf) expression in the rat uterine luminal epithelium. Each uterine cross section of surface epithelium was assessed for intensity of staining scored as O (no stain), 1+ (weak stain), or 2+ (intense stain).

Uterine Ltf Staining

| Group | Diet | Treatment | 0 | 1+ | 2+ |
|---|---|---|---|---|---|
| 1 | Casein | No CEE | 3 | 8 | 0 |
| 3 | Low Soy | No CEE | 10 | 0 | 0 |
| 5 | High Soy | No CEE | 8 | 0 | 0 |
| 7 | Casein | Low CEE | — | — | — |
| 8 | Low Soy | Low CEE | 0 | 8 | 2 |
| 9 | High Soy | Low CEE | 0 | 5 | 5 |
| 10 | Casein | High CEE | 0 | 2 | 7 |
| 11 | Low Soy | High CEE | 0 | 8 | 2 |
| 12 | High Soy | High CEE | 0 | 5 | 3 |

Chi square p = 6 × 10\-12
Combined Groups

| 1 | Casein | No CEE | 3 | 8 | 0 |
| 3,5 | Soy | No CEE | 18 | 0 | 0 |
| 10 | Casein | High CEE | 0 | 2 | 7 |
| 8,9,11,12 | Soy | CEE | 0 | 26 | 12 |

Chi square p = 3 × 10\-13

Figure 3:
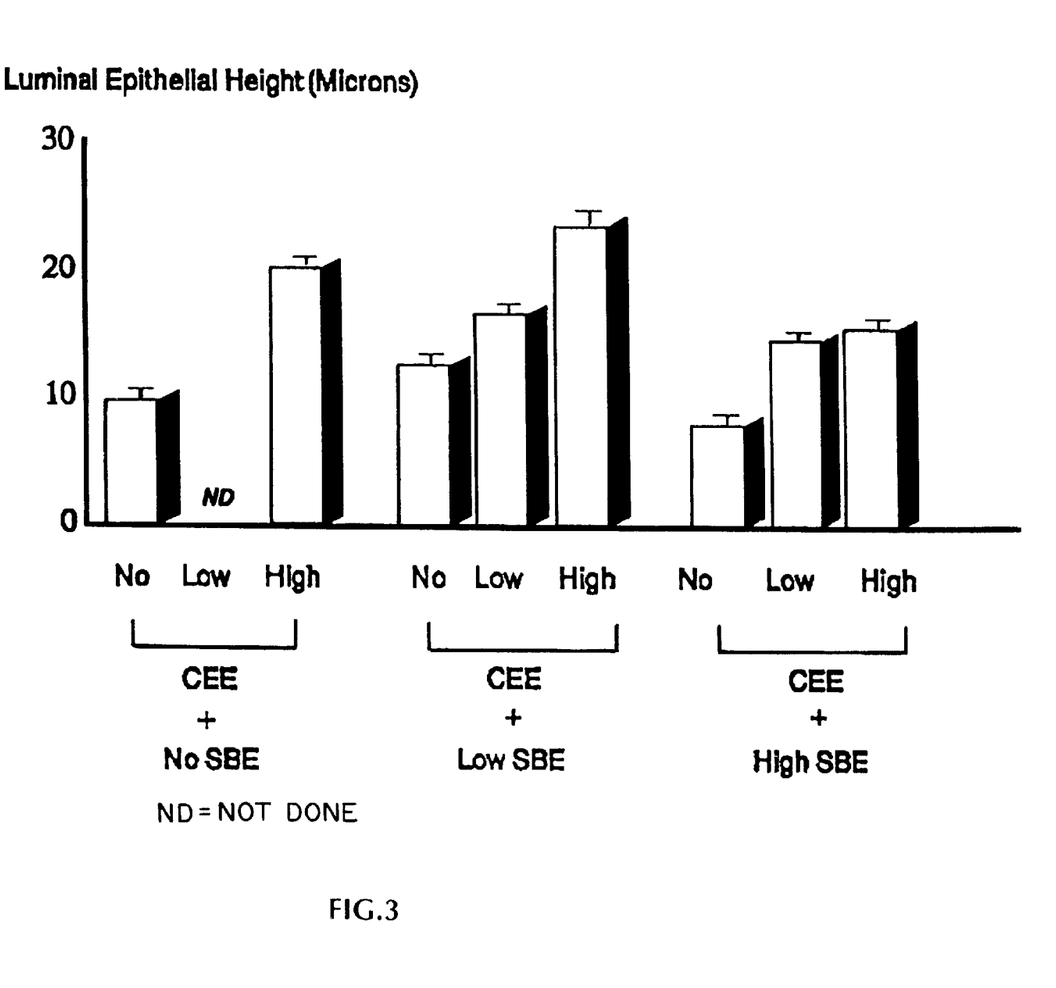
FIG. 3 illustrates the effects of CEE and isoflavones on luminal epithelial height (in microns) in rat uteri (unpublished test results). Error bars indicate the standard error of the mean. ND=not done.

Luminal epithelial height (LEH) measurements in the casein, low and high isoflavone groups were similar, but the addition of CEE to the diets resulted in increased LEH (FIG. 3). The high isoflavone/high CEE group demonstrated a reduction in LEH relative to the high CEE-alone and the low isoflavone/high CEE groups (p<0.05).

Effects of Soy Isoflavones on the Endometrium of Ovariectomized Monkeys

To further assess the possible effects of dietary soy isoflavones on the endometrium, studies were conducted in monkeys that feature dietary trials of these compounds. In a recent study of hormonal replacement therapy and its alternatives [Foth, D. et al, *Am J Clin Nutr.* in press (1997)], adult surgically postmenopausal female macaques were treated continuously with either estradiol (E2), soy protein isolate containing the normal content of isoflavones [Soy(+)], or E2 + Soy(+) for 6 months. Test compounds were administered in the diet, at doses equivalent on a caloric basis to 1 mg/woman/day for estradiol and 148 rng/woman/day for soy isoflavones. Proliferation was assessed by histopathologic, morphometric, and immunohistochemical means in endometrium (data not shown). E2 induced endometrial hyperplasia. Soy(+) alone did not induce endometrial hyperplasia. Endometrial thickness and gland area (as a percentage of total endometrial area) were increased by E2 and E2 + Soy(+). The effects of E2 were partially antagonized by Soy +) (manifested as decreased Ki-67 staining). These results indicate that in this primate model, dietary soy isoflavones have anti-proliferative effects in the endometrium. E2-treated primates supporting the notion that these dietary estrogenic soy isoflavones have a beneficial antagonistic (protective) effect on this target tissue regarding cancer risk.

Discussion

Several markers of estrogen action were used in the ovariectomized rat to assess the independent actions of isoflavones and the interactions of isoflavones with the pharmaceutical mixture of steroidal estrogens, CEE. Similarly, one marker of proliferation was used to assess the effects of isoflavones alone or in combination with E2 on the endometrium of ovariectomized monkeys. To the extent that the endpoint of endometrial proliferation can be considered comparable in the two species, the two models agree well. Uterine weight and vaginal cytology did not demonstrate estrogenic activity of isoflavones at the doses studied in rats in this study, and previous studies in monkeys showed similar results [Anthony, M. S. et al., *J Nutr* 126:43 (1996)]. This is in contrast to earlier studies using uterine weight in mice and rats as biological assays for estrogenic activity in plant materials [Cheng, E. et al, *Ann NY Acad Sci* 61:652 (1955); Bickoff, E. M. et al., *Agr Food Chem,* 10:610 (1962); and Folman, Y. et al., *J Endocrin* 34:215 (1966)]. In those studies, it was shown as early as 1953 that exposure of mice or rats to diets containing phytoestrogens resulted in increased uterine weight; however, these increases occurred at dosages that generally exceeded those used in this study. No estrogenic effects of these doses were found of isoflavones alone in the rat (PCNA and Ltf staining, or LEH) or monkey (Ki-67) models.

Results regarding the interactions of isoflavones and CEE in the rat and isoflavones and E2 in the monkey did show some evidence that the combination of phytoestrogens and steroidal estrogens is additive in effect in the uterus, but only at low doses of steroidal estrogen and high doses of phytoestrogen. In the rat study, all three markers of estrogen action (PCNA, Ltf and LEH) showed evidence of antagonism of CEE stimulation by isoflavones, especially at the high dose. Surprisingly, the exquisitely sensitive marker of uterine estrogen action, Ltf, showed that a weakly estrogenic response was detectable in the rats fed the casein (alone) diet; however this effect was completely absent in rats fed either the low or high isoflavone (alone) diets. Additionally, the potent induction of Ltf by treatment with either dose of CEE was reduced by both the high and low isoflavone diets. These results imply that the endometrial actions of isoflavones in these model systems are that of limited agonism in the milieu of low levels of steroidal hormones, but antagonism at higher levels (ERT replacement levels) of steroidal hormones.

Conclusions

Dietary phytoestrogens affect many physiological processes in mammals. The estrogenic isoflavones are particularly relevant for human health concerns. At present, the emerging impression for menopausal women is enthusiasm regarding potential benefit on risk of several chron "Western" diseases (e.g., breast and endometrial cancers, and cardiovascular disease). The failure of isoflavones to affect vaginal cytology suggests that these compounds would have limited utility in managing the symptoms of atrophic vaginitis in postmenopausal women. On the other hand, the limited estrogen-agonist effects of isoflavones alone on the endometrium, and the partial antagonism of markers of the stimulatory action of steroidal estrogens on the endometrium suggest that the addition of isoflavones to the estrogen replacement therapy of postmenopausal women may be beneficial. In terms of reproductive tract actions in the menopausal women, results in these ovariectomized animal models suggest that soy isoflavones will at least partially antagonize the stimulation of the endometrium by steroidal estrogen, and could thus reduce the risk of endometrial hyperplasia or endometrial cancer in 1) perimenopausal women or menopausal women who might take ERT combined with 2) isoflavones rather than progestins or 3) isoflavones plus a reduced dose or reduced frequency regimen of progestin.

Since these test results indicate that isoflavones (phytoestrogens) have mixed estrogen agonistic and antagonistic actions on the animal uterus, the physiological effects that isoflavones exert on an animal's endometrium are not necessarily predictive of its effects on endometriosis, where human endometrial tissue is located not in the uterus but in the peritoneal cavity. While such animal models may be reasonable to illustrate certain aspects of the human female physiology, the animal models presented are much simpler than the more complicated hormonal events that occur during a normal menstrual cycle in women of child bearing age.

SUMMARY OF THE INVENTION

Currently, there are no hormonal therapies with positive effects on endometriosis without severe side effects and major health concerns. While the detailed unpublished test results provided above (by a co-inventor of the present invention) demonstrate inhibition of endometrial proliferation and antagonism of the stimulatory effects of steroidal estrogens in the endometrium by dietary soy isoflavones, these results in no way teach or suggest the use of soy isoflavones to treat or prevent an unrelated disease, endometriosis. The unpublished test results were based on experiments involving the endometrium, the mucous membrane lining the uterus. In contrast, endometriosis, the subject matter of the present invention, is a disease in which functional and growing endometrial tissue has migrated to areas outside the uterus, typically resulting in severe pain and infertility for the women affected.

In an attempt to develop an alternative therapy having positive therapeutic effects on endometriosis without the debilitating side effects of conventional therapies, the co-inventors of the present invention have discovered several novel methods for the treatment and prevention of endometriosis and related conditions in adult females. In one method of the present invention, at least one naturally-occurring phytoestrogen, in particular isoflavones, is administered in a therapeutically effective dosage to adult females with endometriosis or to females at risk of developing endometriosis.

A second method of the present invention involves the administration of at least one phytoestrogen in combination with at least one hormonal therapeutic agent such as GnRH analogs, androgens, progestins, estrogens or any combination thereof. The therapeutically effective dosage of the phytoestrogen either singly or in combination with other hormonal agents is expected to range between about 25 and about 250 mg/day.

Isoflavones of the preferred type include genistein, daidzein and any metabolic products thereof including conjugates.

In the treatment and prevention of endometriosis, phytoestrogens, in particular soy isoflavones, are administered in therapeutically effective dosages to adult females (humans or animals) diagnosed with endometriosis or experiencing symptoms typically associated with endometriosis such as severe chronic pelvic pain, dysmenorrhea, dyspareunia, abnormal uterine bleeding, infertility, and menstrual cycle-associated rectal bleeding. The preventive aspect of the present invention involves administering therapeutically effective dosages of phytoestrogens to adult females at risk of developing endometriosis including, but not limited to, those females with prior history of endometriosis and/or partial or complete outflow obstruction of the reproductive tract. Other groups of females that are susceptible to the risk of developing endometriosis will be apparent to those skilled in the art.

The term "therapeutically effective dosage" as used in the present invention is defined as the dosage which provides effective treatment or prevention of the above described conditions and/or diseases in females, both humans and animals.

The use of phytoestrogens, particularly isoflavones, either singly or in combination with other hormonal therapies to treat or prevent endometriosis provides distinct advantages over currently administered hormone therapies. First, the present invention is likely to minimize the drug-related side effects that typically lead to non-compliance or untimely termination of treatment. Second, the use of naturally-occurring phytoestrogens overcomes some of the long term health concerns associated with current therapies which, in turn, increases the likelihood that individuals will remain on extended therapeutic regimens for sustained prevention of recurrent disease.

Third, phytoestrogens, particularly soy isoflavones, when administered alone, do not produce the side effects associated with any of the current therapies. More specifically, one of the co-inventors of the present invention has demonstrated antiproliferative actions of isoflavones on endometrium (unpublished results) as well as beneficial effects of isoflavones on other target tissues that are adversely affected by current hormonal therapies, especially cardiovascular effects and vasomotor symptoms Hughes, C. L. et al., Proceedings of the Eighth International Congress on the Menopause, Sydney, Australia, Abstract, (Nov. 1996). Lastly, co-administration of phytoestrogens with a hormonal agent, especially the GnRH analogs, would likely preserve the efficacy of suppression of endometriosis, since the isoflavones have primarily antagonistic effects on the endometrium, but have potent favorable effects on plasma lipids and other cardiovascular risk factors, modest favorable effects on reducing vasomotor symptoms, and possibly beneficial effects on the preservation of bone mass.

The metabolic products of the phytoestrogens contemplated for use in the present invention include equol and conjugates of genistein, daidzein, and other isoflavones. It is further contemplated that any derivative of other phytoestrogens including coumestans and lignans or conjugates thereof may be used in treating or preventing the conditions and/or diseases described hereinabove.

In one aspect of the present invention, a method is disclosed for treating endometriosis in a female, comprising the step of administering to a female having endometriosis or symptoms associated therewith a therapeutically effective dosage of at least one phytoestrogen or a metabolic product thereof.

In another aspect of the present invention, the route of administration for phytoestrogens singly or in combination with other hormonal therapeutic agents is selected from the group of methods consisting of oral, intravenous, parental, transdermal, subcutaneous, intravaginal, intranasal, intrabronchial, and rectal administration.

In yet another aspect of the present invention, the female having endometriosis or a related condition and the female at risk of developing endometriosis is a female of reproductive or post-reproductive age.

In yet another aspect of the present invention, phytoestrogens or a metabolic product thereof are used to prevent endometriosis or related conditions in females.

In another aspect of the present invention, a method is disclosed for treating or preventing endometriosis, comprising administering a therapeutically effective dosage of a preparation comprising at least one phytoestrogen and at least one hormonal therapeutic agent, wherein the phytoestrogen is isoflavone and the hormonal therapeutic agent is selected from the group consisting of GnRH analogs, androgens, progestins, estrogens or any combinations thereof.

The preceding and further objects of the present invention will be appreciated by those of ordinary skill in the art from a reading of the detailed description of the preferred embodiments which follow, such description being merely illustrative of the present invention.

BRIEF DESCRIPTION OF THE DRAWINGS

The invention will be better understood after a reading of the following description of the preferred embodiments when considered with the drawing.

DESCRIPTION OF THE PREFERRED EMBODIMENTS

EXAMPLE 1

Clinical Test Procedures

In accordance with the present invention, the effects of administering a pharmaceutical preparation to females with endometriosis are analyzed. Approximately 400 women that have been diagnosed with endometriosis participate in the study. These women will include those who have presented with symptoms of pelvic pain, completed a pain questionnaire, undergone diagnostic laparoscopy, the diagnosis of endometriosis established and extent of disease documented.

The pharmaceutical preparation comprises at least one naturally-occurring phytoestrogen alone or in combination with at least one hormonal therapeutic agent. Multiple hormones may be used together, for example, estrogens plus progestins in an oral contraceptive preparation. Examples of the types of hormonal therapeutic agents may include, but are not limited to GnRH analogs, androgens, progestins, estrogens or any combinations thereof. The route of administration of the pharmaceutical preparation may vary, which will be discussed below in greater detail.

Phystoestrogens of the type used in the present invention are commercially available, and the conjugates are either commercially available or can be prepared using standard chemical methodology.

Assigned to one of the following treatment groups, each participant is given a 10 ounce soy beverage supplement daily that contains:
1) 20 g soy protein with the isoflavones predominantly extracted (placebo)—control group;

2) 20 g soy protein with about 50 mg of soy isoflavones;

3) 20 g soy protein with the isoflavones predominantly extracted, plus a therapeutic dose of Lupron or GnRH analog or other hormone; or 4) 20 g soy protein with about 50 mg of soy isoflavones plus a therapeutic dose of a GnRH analog or other hormone Following administration of the above dosage regimens to the clinical participants, the expected results are as follows: 1) the control group is miserable and has disease that has either persisted or progressed; 2) the group administered the isoflavones alone has diminished symptomatology over an extended period of time; not a dramatic resolution but gradual, slow improvement; 3) the group administered the Lupron or GnRH analog by itself has a prompt response, but is still feeling miserable because of the menopausal symptoms the drug produces; and 4) the group administered the combination phytoestrogens and GnRH analog has excellent resolution of the disease; the group feels physically well because the phytoestrogens help to control the adverse symptoms of the Lupron; by continuing the phytoestrogens long-term, these individuals will have long-term abatement or suppression of the disease.

While the principal focus of the present invention is the treatment and management of endometriosis externa, such treatment shall also include endometriosis interna (adenomyosis). It is further contemplated that the methods of the present invention will be useful in hormone replacement therapies, female contraception, cancer prevention and treatment of estrogen-dependent malignancies in women, and in cancer prevention and treatment of multiple malignancies in women and men.

EXAMPLE 2

When used in accordance with the present invention, the phytoestrogen alone or in combination with at least one hormone therapeutic agent can be formulated into normal dosage forms such as pills, capsules, tablets, powders, suspensions, emulsions, solutions, syrups, aerosols, soft and hard gelatin capsules, suppositories, injectable solutions, and the like. The phytoestrogen or combination preparation can be administered alone or in combination with pharmaceutically acceptable carriers, diluents, stabilizers, solubilizers, lubricants, binders and the like or excipients thereof. Regardless of the pharmaceutical formulation, the phytoestrogens and/or hormonal agent will be found in a proportion that will impart the desired activity to the female.

Phytoestrogens alone or in combination with other hormonal therapeutic agents may also be injected parenterally, in which case it is administered in the form of a sterile solution containing other components such as glucose or saline. It is further contemplated that administration may be performed transdermally with the use of a transdermal patch or by insertion of subcutaneous implants, each containing the active ingredients and a pharmaceutical carrier. The transdermal patch allows the delivery of the therapeutic preparation to the skin for systemic absorption into the blood stream. Similarly, the subcutaneous implants systematically deliver the preparation into the blood stream.

The dosage requirements for the phytoestrogen alone or in combination with other hormonal agents for administration to females will be based upon dosage requirements to provide adequate suppression of endometriosis with diminished side effects and reduced risks associated with current therapies. The preferred pharmaceutical preparation contains soy isoflavones, like genistein, daidzein or any metabolic conjugates thereof. A wide therapeutic window is contemplated in the present invention based on the daily intake of soy isoflavones in the diet of Oriental women of approximately 25 to about 150 mg/day. In this regard, the proposed treatment and preventive dosages using either a phytoestrogen alone or in combination with other hormonal agents range between about 25 and about 250 mg/day.

Individualization of doses to achieve maximum benefit will be easily accomplished within the wide therapeutic window. Of course, precise dosages for any form of administration to patients will be determined by the administering physician based on their experience with the patient being treated. Generally, phytoestrogens as a single agent or in combination with another hormonal agent should be administered at a concentration that will achieve the desired result without causing any harmful or deleterious side effects.

All references referred to herein are hereby incorporated by reference in their entirety.

It should be understood that various changes and modifications to the presently preferred embodiments described herein will be apparent to those skilled in the art. By way of example, treatment and prevention of endometriosis by phytoestrogens alone or in combination with hormones may improve infertility in women who have endometriosis-associated sub-fertility.

Such changes and modifications can be made without departing from the spirit and scope of the present invention and without diminishing its attendant advantages. It is therefore intended that such changes and modifications be covered by the appended claims.

We claim:

1. A method of treating endometriosis or related conditions in a female, comprising administering to a female having endometriosis or related symptoms a therapeutically effective dosage of at least one phytoestrogen or a metabolic product thereof.

2. The method according to claim 1, wherein the phytoestrogen is an isoflavone, coumestan, lignan or any combination thereof.

3. The method according to claim 2, wherein the preferred isoflavones are soy isoflavones.

4. The method according to claim 3, wherein the soy isoflavone is genistein, daidzein or any metabolic product thereof.

5. The method according to claim 1, wherein at least one phytoestrogen is further combined with at least one hormonal therapeutic agent for administration to the female.

6. The method according to claim 5, wherein at least one hormonal therapeutic agent is a GnRH analog, androgen, progestin, estrogen or any combination thereof.

7. The method according to claim 1, the therapeutically effective dosage of the phytoestrogen ranges between about 25 and about 250 mg/day.

8. The method according to claim 5, wherein the therapeutically effective dosage of the combined phytoestrogen and hormonal therapeutic agent ranges between about 25 and about 250 mg/day.

9. The method according to claim 1, wherein the route of administration is selected from the group of methods consisting of oral, intravenous, parental, transdermal, subcutaneous, intravaginal, intranasal, intrabronchial, and rectal administration.

10. The method according to claim 1, wherein the female is of reproductive or post-reproductive age.

11. The method according to claim 1, wherein the phytoestrogen being administered is in a form selected from the group consisting of pills, capsules, tablets, powders, suspensions, emulsions, solutions, syrups, aerosols, soft and hard gelatin capsules, suppositories, injectable solutions, and the like.

12. The method according to claim 5, wherein the combination of phytoestrogen and hormonal therapeutic agent being administered is in a form selected from the group consisting of pills, capsules, tablets, powders, suspensions, emulsions, solutions, syrups, aerosols, soft and hard gelatin capsules, suppositories, injectable solutions, and the like.

13. A method of preventing endometriosis and other related disorders in a female, comprising administering to a female at risk of developing or suffering recurrence of endometriosis or other related conditions a therapeutically effective dosage of at least one phytoestrogen or a metabolic product thereof.

14. The method according to claim 13, wherein the phytoestrogen is an isoflavone, coumestan, lignan or any combination thereof.

15. The method according to claim 14, wherein the preferred isoflavones are soy isoflavones.

16. The method according to claim 15, wherein the soy isoflavone is genistein, daidzein or any metabolic products thereof.

17. The method according to claim 13, wherein at least one phytoestrogen is further combined with at least one hormonal therapeutic agent for administration to the female.

18. The method according to claim 17, wherein at least one hormonal therapeutic agent is a GnRH analog, androgen, progestin, estrogen or any combination thereof.

19. The method according to claim 13, wherein the therapeutically effective dosage of the phytoestrogen ranges between about 25 and about 250 mg/day.

20. The method according to claim 17, wherein the therapeutically effective dosage of the combined phytoestrogen and hormonal therapeutic agent ranges between about 25 and about 250 mg/day.

21. The method according to claim 13, wherein the female is of adolescent (pre-reproductive), reproductive or post-reproductive age.

22. The method according to claim 13, wherein the route of administration is selected from the group of methods consisting of oral, intravenous, parental, transdermal, subcutaneous, intravaginal, intranasal, intrabronchial, and rectal administration.

23. The method according to claim 13, wherein the phytoestrogen being administered is in a form selected from the group consisting of pills, capsules, tablets, powders, suspensions, emulsions, solutions, syrups, aerosols, soft and hard gelatin capsules, suppositories, injectable solutions, and the like.

24. The method according to claim 17, wherein the combination of phytoestrogen and hormonal therapeutic agent being administered is in a form selected from the group consisting of pills, capsules, tablets, powders, suspensions, emulsions, solutions, syrups, aerosols, soft and hard gelatin capsules, suppositories, injectable solutions, and the like.

25. A method for treating or preventing endometriosis or other related symptoms or conditions, comprising administering a therapeutically effective dosage of a preparation comprising at least one phytoestrogen and at least one hormonal therapeutic agent, wherein the phytoestrogen is selected from the group consisting of isoflavones, coumestans, lignans or any combination thereof and the hormonal therapeutic agent is selected from the group consisting of GnRH analogs, androgens, progestins, estrogens or any combinations thereof.

\* \* \* \* \*

UNITED STATES PATENT AND TRADEMARK OFFICE
CERTIFICATE OF CORRECTION

Patent No.: 5,942,539
Dated: August 24, 1999
Inventors: Claude L. Hughes, Jr., et al.

It is certified that errors appear in the above-identified patent and that said Letters Patent is hereby corrected as shown below:

column 1, insert the following paragraph after the title of the invention:

--STATEMENT REGARDING FEDERALLY SPONSORED RESEARCH

This invention was made with U.S. government support from a grant funded by the U.S. Army USAMRAA Contract DAMD 17-94-J-4201. The U.S. government may have certain rights in the invention.--
 column 6, line 30, delete "." after "4°C";
 column 6, line 35, delete "Pa." and insert --PA--;
 column 6, line 43, delete "." after "35°C";
 column 6, line 45, delete "Calif." and insert --CA--;
 column 6, line 59, delete "Md." and insert --MD--;
 column 7, line 13, delete "endometrlal" and insert --endometrial--; and
 column 7, lines 53-54, delete "expresslon" and insert--expression--.

Signed and Sealed this

Sixth Day of June, 2000

Q. TODD DICKINSON

*Attest:*

*Attesting Officer*  *Director of Patents and Trademarks*